United States Patent [19]

Maurer

[11] Patent Number: 4,556,051

[45] Date of Patent: Dec. 3, 1985

[54] METHOD AND APPARATUS FOR HEALING TISSUE

[75] Inventor: Donald D. Maurer, Anoka, Minn.

[73] Assignee: EMPI, Inc., Fridley, Minn.

[21] Appl. No.: 439,357

[22] Filed: Nov. 5, 1982

[51] Int. Cl.[4] ............. A61N 1/32; A61N 1/42
[52] U.S. Cl. .................. 128/1.5; 128/419 F; 128/421; 128/798
[58] Field of Search .......... 128/1.3, 1.5, 419 F, 128/420 R, 420 A, 798, 802, 804, 421, 422, 423

[56] References Cited

U.S. PATENT DOCUMENTS

| | | | |
|---|---|---|---|
| 3,915,151 | 10/1975 | Kraus | 128/1.5 |
| 4,197,851 | 4/1980 | Fellus | 128/798 X |
| 4,248,247 | 2/1981 | Ware et al. | 128/798 |
| 4,266,532 | 5/1981 | Ryaby et al. | 128/1.5 |
| 4,266,533 | 5/1981 | Ryaby et al. | 128/1.5 |
| 4,315,503 | 2/1982 | Ryaby et al. | 128/1.5 |
| 4,391,270 | 7/1983 | Uragami | 128/1.3 |
| 4,454,883 | 6/1984 | Fellus | 128/1.5 X |

FOREIGN PATENT DOCUMENTS 860767  9/1981  U.S.S.R. ............... 128/1.3

*Primary Examiner*—Lee S. Cohen
*Attorney, Agent, or Firm*—Kinney & Lange

[57] ABSTRACT

An apparatus and method for promoting healing of injured tissue, such as fractured bone, with interacting electric current and a magnetic flux field. Electrodes are adhesively attached to the skin adjacent the injured tissue. One or more coil assemblies normally spaced from the electrodes are located adjacent the tissue in alignment with the fractured bone. A current generator electrically connected to the electrodes operates to provide electric current pulses to the electrodes. A field generator electrically connected to the coil assemblies is operable to energize the coil assemblies to produce magnetic field pulses. The pulse generator and field generator are electrically coupled to maintain the electrode current pulses and magnetic field pulses in fixed phase relationship to produce a net current in the region of the fractured bone and generally perpendicular to the plane of the fracture.

28 Claims, 14 Drawing Figures

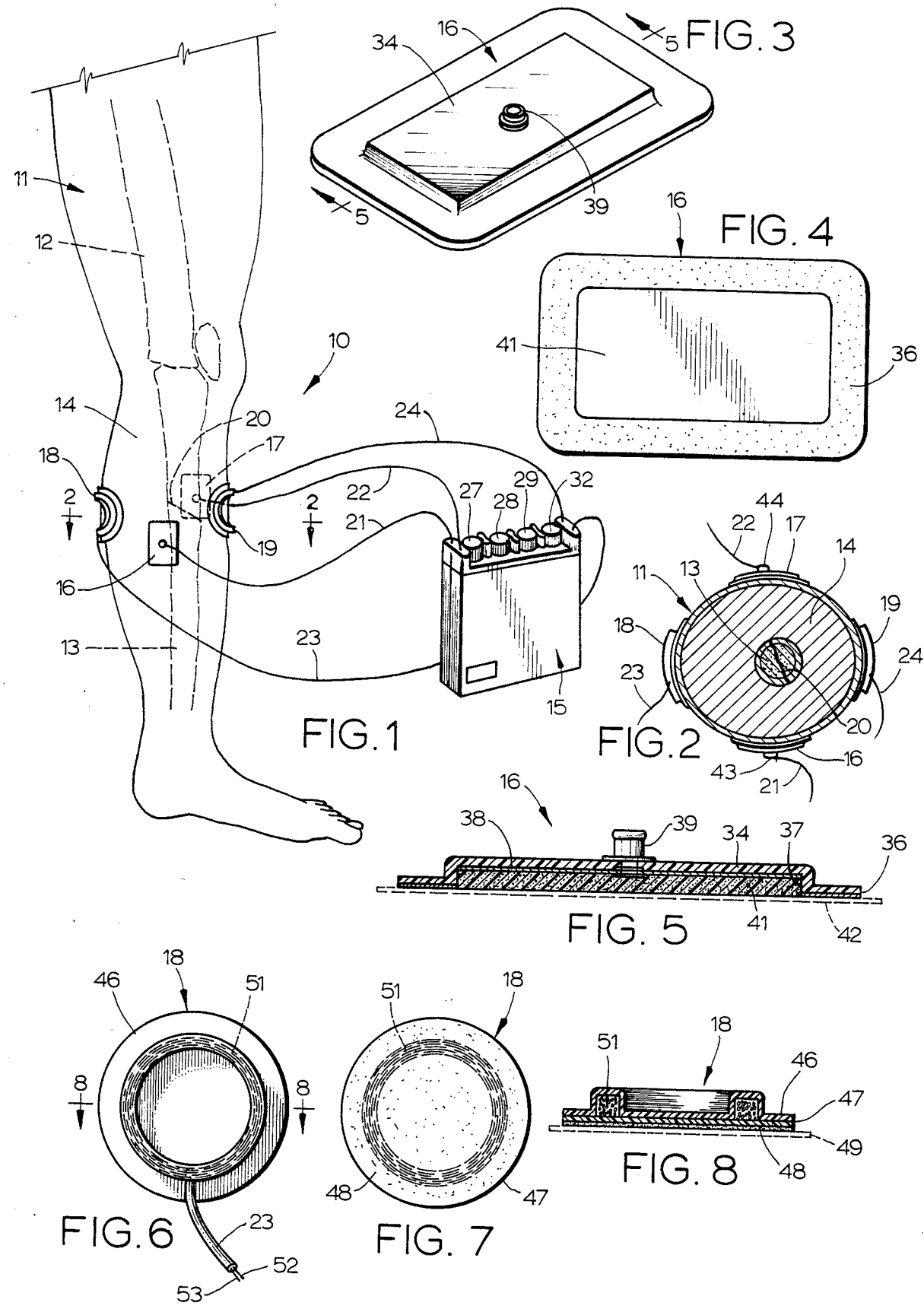

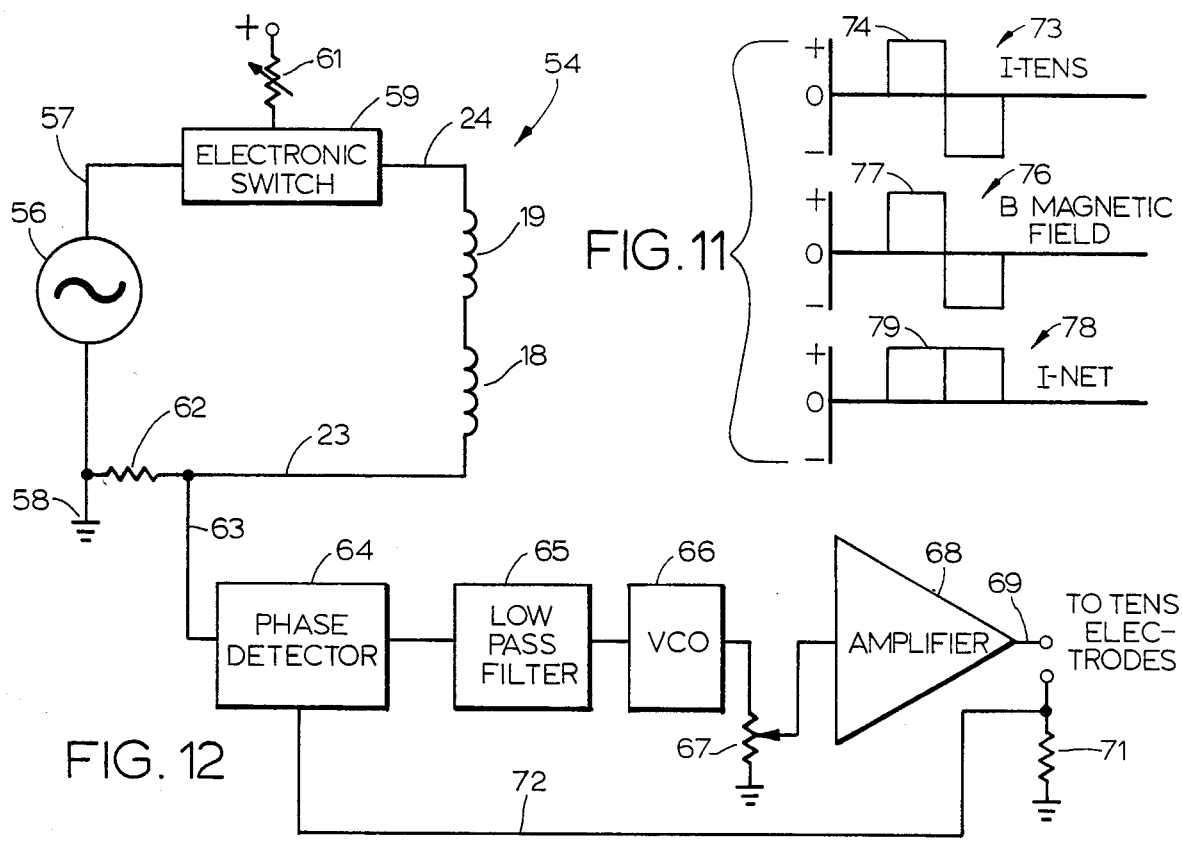
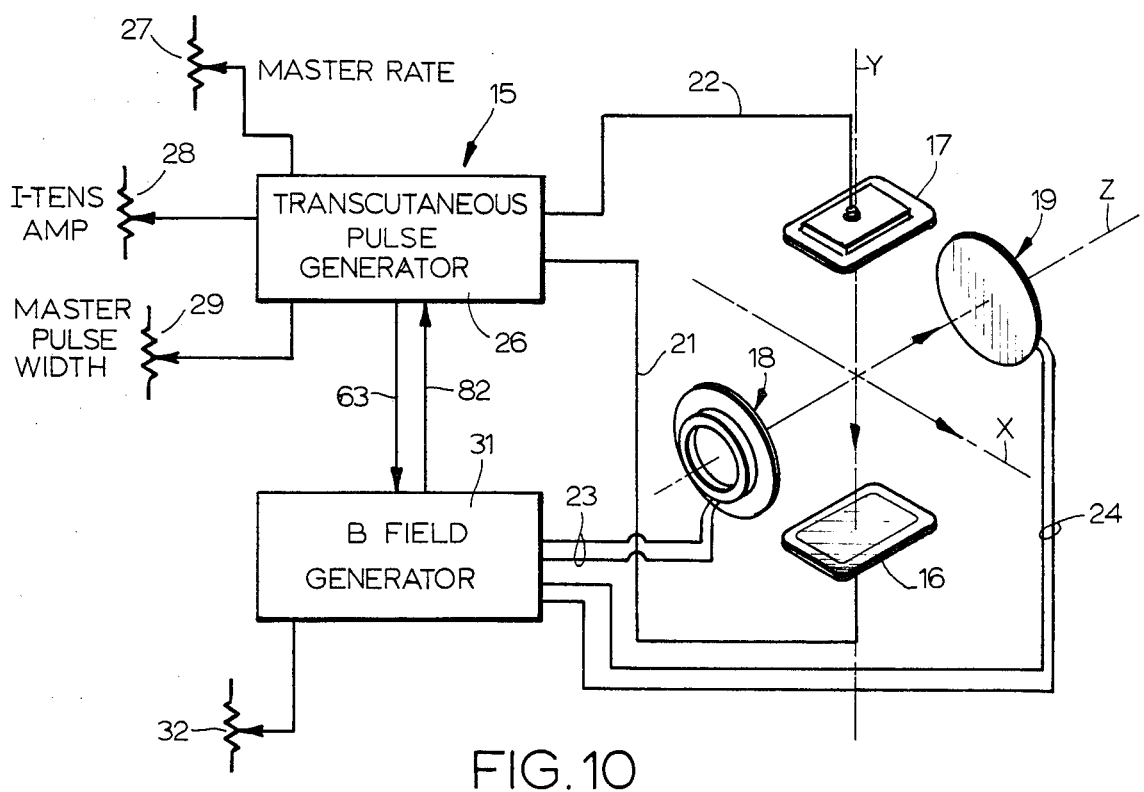

4,556,051

METHOD AND APPARATUS FOR HEALING TISSUE

BACKGROUND OF INVENTION

It is known that changing the electrical and/or electrical chemical environment of living tissue causes a modification of the growth, repair, and maintenance behavior of the tissue. The modification is carried out by subjecting the tissue to electrical voltage and current. One method of changing the electrical environment comprises the use of a 1-15 microampere constant current source across a bone fracture. Metal electrodes are used to transmit the current. Clinical evidence demonstrates acceleration of ossification or bone fracture healing. Another method of altering the electrical environment is the use of induced currents from the outside of the body via magnetic pulses from externally applied coils. The coils induce current in the conductive environment of the tissue and thereby create healing effects by altering the effective current in the tissue at the bone fracture site.

Various duty cycles and frequencies are critical in achieving bone healing in the implementation of the magnetically induced current method. Ion mobility and distance of travel across the fracture dictates the net energy required over time. Due to the restrictive nature of the implementation of the induced currents by a pulsed magnetic field, specific parameters of ON time, OFF time, and the asymmetry of the positive and negative portions of the pulse wave determine the net energy over time in any one direction. This restricts the magnetic-induced method to a very limited range which may not necessarily be biologically optimum for the particular patient's condition. The magnetic-induced method is advantageous in that the currents are induced throughout the region of the treatment, rather than confined to the fracture site. The dispersion of the current induced in the region may of necessity effect the blood flow in the region with subsequent beneficial results. Bone fracture healing is also enhanced due to the charged nature of proteins and extra cellular fluids.

Ryaby and Pilla in U.S. Pat. Nos. 4,266,533 and 4,315,503 disclose a method and apparatus for enhancing the growth, repair, and maintenance of living tissues by applying pulse wave forms of voltage and current of specific timed frequency amplitude relations to the tissue. A varying electro-magnetic field is inductively coupled through direct induction into or upon the tissue under treatment. The information furnished to the tissue is designed to influence the behavior of the non-excitable cells, such as those involved in tissue growth, repair, and maintenance.

Kraus discloses in U.S. Pat. No. 3,915,151 an apparatus for promoting healing of bone tissue with the use of a coil to produce a magnetic field within the region to be treated and sheet-like electrodes associated with the coil to produce an electrical field to influence the recovery of the structure of the damaged bone tissue.

SUMMARY OF INVENTION

The invention is directed to an apparatus and method for promoting healing of body tissue, such as a fracture in a bone of a primate or animal. The apparatus is useable to treat other parts of the body, such as hip fractures, to promote the healing of the fractures. The method is a non-intrusive treatment utilizing electrode means attached to the skin of the patient adjacent the fracture of a bone and coil means located adjacent the skin and the fracture. The electrode means and coil means are used to establish interacting electric and magnetic fields to enhance tissue healing. The coil means is angularly spaced from the electrode means. The electric generator means is electrically connected to the electrode means and the coil means to provide current pulses to the electrode means and coil means. The energized coil means establishes a pulsed magnetic field. The current pulses and the pulsed magnetic field are in a phase relationship with each other so as to produce a unidirectional net current along the length of the bone and through the region of the injured tissue. The unidirectional current flows generally perpendicular to the surface of the fracture and is of a magnitude and duration appropriate to the specific ion or cellular charge and mobility. The apparatus is amenable to portability, as the net current is the sum of the electrode current and the current originating from the magnetic flux field of the coil means. The control point of the maximum current can be varied by changing the location of the electrodes and coil means relative to the fracture and relative to each other. This provides the apparatus with versatility and utility.

In one embodiment of the apparatus of the invention, a pair of electrodes are attached to opposite sides of the skin of a patient in lateral alignment with the fracture of a bone. The electrodes are self-adhering electrodes that are attachable to a pulse generator means operable to provide electric current pulses to the electrodes. The pulse generator means has separate adjustable means operable to control rate, width, and amplitude of the electric pulses. A pair of coil assemblies circumferentially oriented about 90 degrees relative to the electrodes are located adjacent the skin in alignment with the fracture. Each coil assembly is flexible and has means for attaching the coil assembly to the patient. Each coil assembly has a coil connected to field generator means operable to provide electric current pulses to the coil to establish a magnetic flux field. The total magnetic flux field is the sum of both fields of the coil assemblies. This provides a uniform magnetic field in the bone fracture area. The field generator means has an adjustable absolute limit field intensity control that is operable independently of the adjustable means of the pulse generator means. The master pulse rate control of the pulse generator means sets the pulse interval of both the electrode current and the magnetic field. The amplitude control of the pulse generator means sets the intensity of the electrode current and in a tracking manner the magnetic field.

The pulse generator means and field generator means are electrically coupled to each other with phase synchronization circuit means operable to keep the current and magnetic field pulses in a fixed phase relationship so that the current pulses and the magnetic coil field pulses produce a net current in the direction of the length of the fractured bone, perpendicular to the fracture surface. This net current has substantial beneficial tissue healing enhancement characteristics.

The invention includes the method of enhancing the healing of tissue, such as fractured bone tissue. Sequential pulses of electrical current are continuously applied to the skin of the body adjacent to the injured tissue. A pulsed magnetic field is simultaneously applied to the skin of the body adjacent the injured tissue and spaced from the area of application of the pulses of electrical current. The pulsed magnetic field and the pulses of electric current are in relative time phase to produce a unidirectional net current along the longitudinal path of the injured tissue and generally parallel to the injury whereby the growth and repair behavior of the injured tissue is modified to enhance the healing thereof. Preferably, the pulses of electric current are applied to opposite first portions of the skin and aligned with the injured tissue, such as a bone fracture. The magnetic field is established with coil assemblies located adjacent opposite second portions of the skin and laterally aligned with the injured tissue. The coil assemblies are located about 90 degrees relative to electrodes used to transmit the current pulses to the tissue.

The method of enhancing the healing of tissue, such as a fractured bone, is not restricted to pulsed electric currents and varying magnetic flux fields. Where constant, uninterrupted currents are required, the apparatus can be switched to a mode whereby a static magnetic flux field is created by constantly energizing the coil assemblies. Alternatively, a static magnetic flux field can be created with the use of one or more permanent magnets. A direct current is provided to the electrodes simultaneously with the energization of the coil assemblies. The resultant net current flows generally perpendicular to the surface of the fracture. The net current has substantial beneficial healing enhancement characteristics.

The coil means includes a pair of coil units or assemblies for providing a magnetic flux field in living tissue. Each coil assembly has flexible body means having a surface accommodating means, such as an adhesive layer, for attaching the body means to the skin of the tissue. A coil, such as a plurality of turns of wire, is located within the flexible body means. The coil, when connected to an electrical power supply, establishes a magnetic flux field in the living tissue. The flexible body means in one form of the coil assembly comprises a flexible first sheet member having a first surface and a second surface. The attaching means covers the second surface to attach the assembly to the skin tissue. A coil comprising a plurality of turns of wire is located adjacent the first surface. A second flexible sheet member covers the coil and is secured to the first sheet member to enclose the coil between the first and second sheet members. The coil is connectable to electrical conductors leading to the field generator. The coil assembly is a flexible one-piece unit that can be bent to conform to the curvature of the skin, such as the skin of a leg.

In a second embodiment of the apparatus of the invention, a pair of electrodes are attached to opposite sides of the skin of a patient in alignment with the injured tissue, such as a fracture of a bone. A pulse generator means having separable adjustable means operable to control pulse rate, width and amplitude is electrically coupled to each electrode. A coil assembly is located adjacent the patient in alignment with the fracture intermediate the pair of electrodes. Preferably, the coil assembly is located about 90 degrees from each electrode. The coil assembly is connected to a field generator means operable to provide electric current pulses to the coil to establish a magnetic flux field. The field generator means and pulse generator means are coupled in pulsed synchronization so that the current pulses and the pulsed magnetic field are in a fixed phased relationship with each other, so as to produce unidirectional net current along the length of the bone and through the region of the injured tissue or bone fracture.

IN THE DRAWINGS

FIG. 1 is a diagrammatic view of a primate leg having a fractured tibia treated with the method and apparatus for healing tissue of the invention;

FIG. 2 is an enlarged sectional view taken along the line 2—2 of FIG. 1;

FIG. 3 is a perspective view of an electrode of the apparatus removed from the skin of the leg;

FIG. 4 is an enlarged bottom view of the electrode of FIG. 3;

FIG. 5 is an enlarged sectional view taken along the line 5—5 of FIG. 3;

FIG. 6 is an enlarged top plan view of a coil assembly of the apparatus of FIG. 1 removed from the leg;

FIG. 7 is a bottom plan view of the coil assembly of FIG. 6;

FIG. 8 is an enlarged sectional view taken along the line 8—8 of FIG. 6;

FIG. 10 is a block diagram of the tissue healing apparatus of the invention;

FIG. 11 shows diagrams illustrating current wave shape, synchronized magnetic field, and net current resulting from the apparatus of the invention;

FIG. 12 is a circuit diagram of a coil assembly circuit with transcutaneous current pulses having a phase relationship to the magnetic field via a phase locked loop;

DESCRIPTION OF PREFERRED EMBODIMENTS

Figure 9:
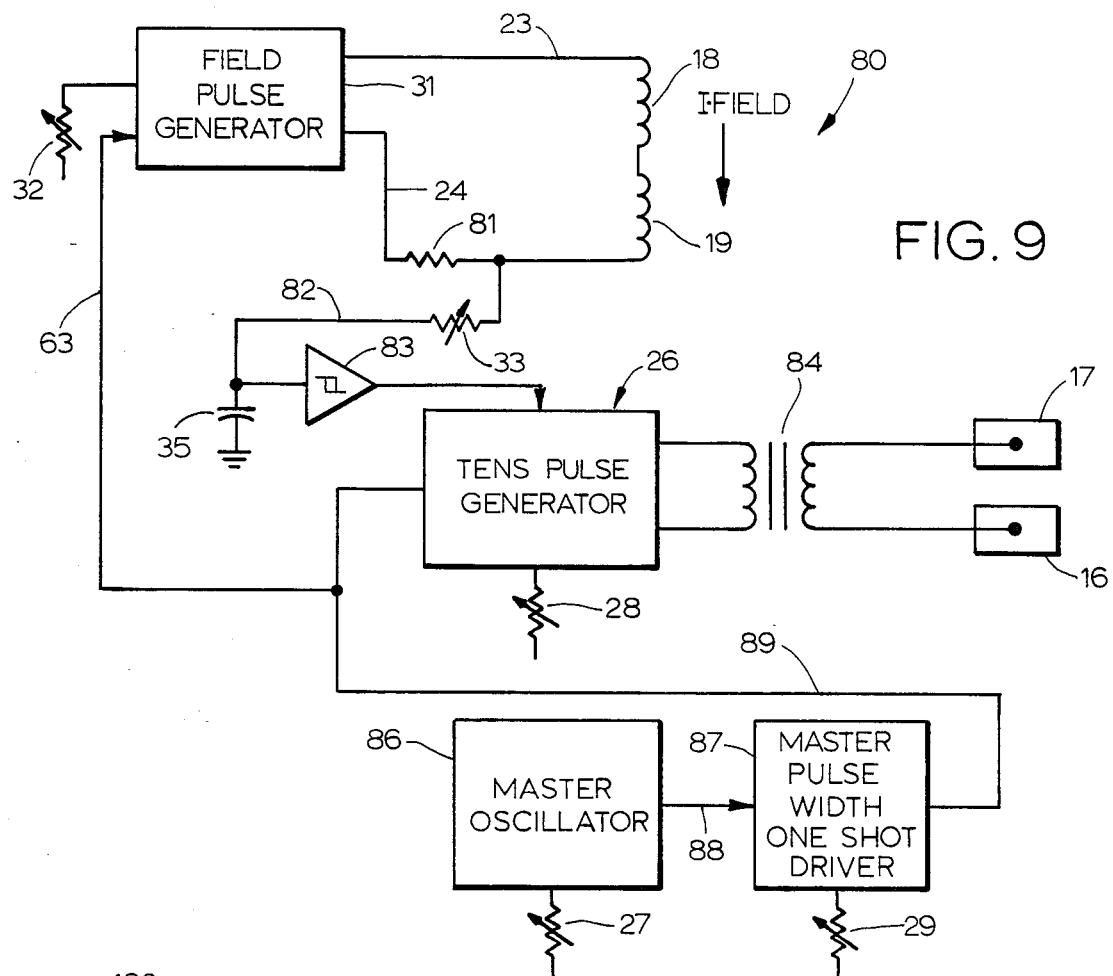
FIG. 9 is a circuit diagram of the coil assembly and electrode circuits showing pulse synchronization.

Referring to FIGS. 1 and 2, there is shown the apparatus of the invention indicated generally at 10 providing electrical treatment for enhancing healing of bone tissue and implementing the method for healing injured tissue of the invention. Apparatus 10 is connected to a primate leg 11. Primate leg 11 has the thigh bone or femur 12 articulately joined to the shin bone or tibia 13. Leg 11 has muscle and skin tissue 14 surrounding bones 12 and 13. Apparatus 10 has a power generator unit indicated generally at 15 electrically coupled to electrodes 16 and 17 adhesively attached to opposite sides of leg 11 in transverse alignment with a fracture 20 of tibia 13. Electrical conductors 21 and 22 connect output terminals of power generator unit 15 to electrodes 16 and 17. A first coil unit or assembly 18 is adhesively secured to the back of leg 11 midway between the electrodes 16 and 17. Coil 18 is in general transverse lateral alignment with fracture 20 and electrodes 16 and 17. Coil 19 is positioned on the other side of the leg, opposite to coil 18. Electrical conductor cables 23, 24 electrically connect coil assemblies 18 and 19 to a field generator 31 incorporated in power generator unit 15. As shown in FIG. 1, the pulse generator and field generator are contained in a portable box housing having a top accommodating control for these generators.

Referring to FIGS. 1 and 10, power generator unit 15 has a transcutaneous pulse generator 26 having three manually operated controls comprising a pulse rate control 27, an amperage control 28, and a pulse width control 29. Pulse generator 26 can be the stimulation device disclosed by Maurer in U.S. Pat. No. 4,340,063.

The disclosure of U.S. Pat. No. 4,340,063 is incorporated herein by reference. Power generator unit 15 includes a magnetic field generator 31 having a manually operated field magnitude control 32 that is operable independently of the controls of the pulse generator 26. Pulse generator 26 is electrically coupled with line 63 to field generator 31 to synchronize the operation of generators 26 and 31, as hereinafter described. The adjustment of pulse rate control 27 sets the pulse intervals of both the electrode current and the magnetic field. The adjustment of amplitude control 28 sets the intensity of the electrode current and in a tracking manner the magnetic field. The magnetic field control 32 is used to adjust the limit of the intensity of the magnetic field. Control 32 allows the adjustment of greater magnetic field intensities than the electrode current intensities, as the electrode current intensities should be kept below the intensity that produces local skin sensations.

Referring to FIGS. 3–5, there is shown a disposable electrode indicated generally at 16 adapted to be adhesively attached to skin tissue 14 adjacent fracture 20. Electrode 17 is identical to electrode 16. The following description is limited to electrode 16. Electrode 16 has a structural outer sheet member 34, such as a plastic adhesive tape having a layer of adhesive 36 on a generally rectangular inner surface surrounding a rectangular recess 37. A metal sheet or foil 38 is located in the base of the recess 37. Foil 38 has a generally rectangular shape of a size that fits in recess 37 and covers the inside of member 34 forming the base of recess 37. Foil 38 is a flexible electrically conductive material, such as aluminum, tin, stainless steel, or silver. The center portion of foil 38 is attached to an upwardly directed snap button 39. Button 39 projects upwardly through the center of sheet member 34 and terminates in an upper end having an annular outwardly directed bead. A rectangular pad 41 of an adhesive electrically conductive polymer is located in surface engagement with metal foil 38 in recess 37. The material of pad 41 can be the electrically conductive adhesive disclosed in U.S. Pat. No. 4,248,247. The flat upper surface of pad 41 is surface bonded to the entire surface of foil 38 to insure uniform current density over the area of the electrode pad 41. Pad 41 has a generally flat lower or outside surface adapted to be located in surface engagement with the skin of leg 11. The lower or skin contact surface of pad 41 is in general alignment with the rectangular adhesive layer 36 on sheet member 34. Pad 41 is a generally rectangular electrode having a length about two times its width. The electrode pad 41 is compatible with the skin tissue and adheres in surface contact to the skin to provide a surface electrical contact with the skin of leg 11. Electrode pad 41, being in surface contact with foil 38, has a uniform current density and structural integrity. Adhesive layer 36 and electrode pad 41 are protected with a removable protective release paper 42. In use, release paper 42 is removed from the adhesive layer 36 and electrode pad 41 prior to the mounting of the electrode 16 on leg 11. Preferably, electrode 16 is located in longitudinal alignment with tibia 13 adjacent fracture 20. Both electrodes 16 and 17 are located in longitudinal alignment with tibia 13, as shown in FIG. 1. Electrodes 16 and 17 are positioned on diametrically opposite sides of leg 11. As shown in FIG. 2, tibia 13 is located about midway between electrodes 16 and 17. Electrodes 16 and 17 are self-adherent electrodes applied directly to the skin of the patient. They are held in place by the adhesive property of electrode pad 41, as well as adhesive 36. In fractures that require a cast, windows are provided in the cast. The electrodes 16 and 17 are applied through the windows directly to the skin of the patient. A snap cap 43 electrically couples the line 21 to button 39. Snap cap 43 is removable from button 39, whereby the electrode 16 can be replaced with a new electrode. A snap cap 44 connects line 22 to electrode 17. Cap 44 is removably attached to the button of electrode 17.

Referring to FIGS. 6–8, there is shown a coil assembly or unit 18, used with apparatus 10 in FIG. 1 to generate a magnetic field which establishes and controls the direction of flow of electric current in tibia 13. Preferably, the net current flows along the length of the bone in a direction generally perpendicular to the fracture plane 20. Coil unit 19 is identical to coil assembly 18. Coil assembly 18 has a flexible outer sheet member, such as a plastic tape 46, mounted on a circular plastic base or inner sheet member 47. Base 47 has a continuous inside surface supporting a layer of adhesive 48. As shown in FIG. 8, a sheet of release paper 49 covers adhesive 48. In use, the release paper 49 is peeled off so that adhesive 48 can be used to support coil assembly 18 on a surface, such as the skin of leg 11.

A circular coil 51 is contained between sheet member 46 and base 47. Sheet member 46 has an annular chamber or channel accommodating coil 51. Coil 51 comprises a plurality of turns of electrically conductive wire. The number of turns of wire can vary to provide the coil with different magnetic field intensities. Coil 51 is connected to a pair of conductor lines 52 and 53 located within cable 23. Lines 52 and 53 are connected to opposite ends of coil 51 with conventional male-female electrical connectors. Coil 51 is hermetically sealed between sheet members 46 and 47. Sheet members 46 and 47 can be plastic sheets that are heat sealed together. Coil assembly 18 is a one-piece unit that can be flexed or shaped to conform to the curvature of a portion of the body, such as leg 11. Coil 51 can be encapsulated into a flexible body of plastic having a generally flat surface accommodating adhesive 48. In an example of coil assembly 18, sheet member 46 and base 47 are circular having a diameter of 10 cm. The height of the coil assembly is 1 cm. Coil 51 has 100 turns of insulated No. 17 wire. Coil assembly 18 can have other numbers of wire turns and different types of wire. Coil assemblies 18 and 19 can be replaced with coils applied to a band or strap having a releasable fastener, such as a Velcro-type fastener. The coils are attached to the band with adhesive strips or sheet members. In use, the band is wrapped around the portion of the body, such as the leg of a patient, to locate the coils relative to the bone fracture and the electrodes 16 and 17. An example of this type of coil support structure is shown by Ryaby in U.S. Pat. No. 4,266,532.

Referring to FIG. 9, there is shown an electrical circuit diagram 80 coupling TENS pulsed generator 26 which provides electrical current to electrodes 16 and 17 with field generator 31 operable to provide pulsed electrical current to coil assemblies 18 and 19, providing pulsed synchronization of the current pulse outputs of generators 26 and 31. The electrical circuit of the field pulse generator 31 and coil assemblies 18 and 19 includes a resistor 81. A line 82 couples line 24 of the field generator circuit to transcutaneous pulsed generator 26. An amplifier or Schmitt trigger 83 interposed in line 82 functions to trigger or gate the output of the transcutaneous pulse generator 26 in a fixed phase relationship with the magnetic flux field generated by coil assemblies 18 and 19. The phase may be adjusted by control 33 acting in conjunction with capacitor 35. The output of the transcutaneous pulsed generator 26 is transmitted via transformer 84 to electrodes 16 and 17.

The adjustment of the amplitude control 28 sets the intensity of the electrode current and in a tracking manner the magnetic field established by coil assemblies 18 and 19. A master oscillator 86 sets the pulse intervals of both the electrode current and the magnetic field. The adjustment of the pulse rate is achieved through a variable control 27. Oscillator 86 is connected in series to a master pulse width one shot driver 87 with line 88. Variable control 29 is used to adjust the pulse width. The output of drive 87 is coupled to the transcutaneous pulse generator 26 with line 89 and the field generator 31 via line 63.

Referring to FIG. 10, the coordinate system of the magnetic field and electric current on bone 13 is shown as X, Y, and Z vectors. Electrodes 16 and 17 are located along the Y vector on opposite sides of leg 11 in alignment with fracture 20. Coil assemblies 18 and 19 are located along the Z vector on the front and rear portions of leg 11 in alignment with fracture 20. The X vector is located 90 degrees with respect to the Y and Z vectors. The longitudinal axis of bone 13 coincides with the X vector in the coordinated system. Fracture 20 of bone 13 intersects the juncture of the X, Y, and Z vectors. The net force produced by the electrode current and magnetic field acting on ions in the intercellular fluid is at right angles to both the magnetic field and the direction of current flow. The net force is in the direction of the X vector. Coil assemblies 18 and 19 being positioned across from each other are excited in such a fashion that the resulting magnetic field is the sum of both fields of the coil assemblies 18 and 19. This provides a more uniform magnetic field in the bone fracture area. The parameters of the coil assemblies 18 and 19 are determined by the necessary magnetic field flux in the bone fracture area to achieve optimum healing conditions. As an example, a suitable coil assembly would have the following parameters: the wire coil 51 has a mean diameter of 7.5 cm, 80–100 turns of wire, and wire size No. 17. The coil is enclosed in a flexible plastic body. The body has a surface accommodating an adhesive for holding the body on the skin of a patient.

The apparatus can accommodate additional coil assemblies and electrodes suitably mounted on the leg to interact properly. The exact physical relationship of the coil assemblies 18 and 19 relative to electrodes 16 and 17 is not restricted to 90 degrees. Advantageous tissue healing results can be achieved at angles less than 90 degrees between electrodes and coil assemblies. Preferably, the 90-degree orientation between the electrodes and coil assemblies provides an optimum bone tissue healing environment.

The net current, which is in the preferred direction X, i.e., perpendicular to the fracture plane, results from Lorentz force on the free charges produced as a result of the interaction of the current applied externally by electrodes 16 and 17 and by magnetic field produced by coil units 18 and 19. An additional benefit of these Lorentz forces is a mechanical pumping action of the ionic fluids of both polarities in a direction across the fracture site to cause increased metabolic action across the fracture.

The Lorentz forces are governed by the equation:

$$F = I\, l\, B\, \sin\theta$$

where
I is the intensity of the current
B is the magnetic field intensity
l is the path length of current carriers under consideration
$\theta$ is the angle between the magnetic field intensity and direction of current carriers.

Thus, since the individual ionic charge carriers have different mobilities, but opposite direction, they tend to both migrate in the same direction in the extra cellular fluid at different velocity. Thus, a charge or electrical potential difference results and a fluid concentration of ions occurs within the extra cellular fluid. Pulse generator 26 and field generator 31 pulse the electrical current to electrodes 16 and 17 and the coil units 18 and 19 to allow maximum energy efficiency and to avoid skin burns from direct currents. Preferably, bidirectional currents and magnetic fields are provided to avoid polarity effects from the transcutaneous current producing device or generator 26 and to increase the efficiency, since the net effect is double the current internally along tibia 13. This has the additional desirable advantage of reducing the current available that stimulates superficial skin senses.

Referring to FIG. 11, there is shown the graphic representation of the bidirectional square wave form currents and fields achieved by apparatus 10 in order to avoid polarity effects from the pulse generator 26 and to increase the efficiency of the apparatus. The net effect is to double the current internally along fracture 20, while halving the current available to stimulate superficial skin senses. Graph 73 shows the current square wave form 74 transmitted from pulse generator 26 to electrodes 16 and 17. The graphic representation 76 shows the magnetic field square wave form 77 produced by coil assemblies 18 and 19. The magnetic field wave form 77 has a fixed phase relationship with current wave form 74. The combination of magnetic field wave form 77 and current wave form 74 produces a net current 79. The multiplication of the current is particularly useful in surface wound healing, since the optimum direction of current is easily controlled. This control cannot be achieved with the use of surface electrodes, per se.

A variety of different wave forms can be produced by suitable pulse generators and field generators. For example, ramp-type wave shapes can be produced to cause a double saw tooth net current. Modified trapezoidal wave shapes can be produced by a pulse generator and field generator. The square wave forms are preferred, as they result in greater efficiency and electrical circuit simplicity.

As an alternative to the pulsed method of energizing the coil assemblies 18 and 19 and electrodes 16 and 17, as shown in FIG. 10, sinusoidal waves in the frequency ranging from 10 Hertz to hundreds of KHz can be used to energize coil assemblies 18 and 19 and electrodes 16 and 17. When sine waves are used, it is necessary to lock the phase of the electrode stimulation sinusoidal to that of the coil assemblies, since the coil assemblies will cause a phase lag on the current to voltage.

Referring to FIG. 12, there is shown an electrical circuit indicated generally at 54 for synchronizing the energization of coil assemblies 18 and 19 with the current pulses applied to electrodes 16 and 17 to provide a net current in tibia 13. Circuit 54 has a sinusoidal excitor or sine wave power source 56 coupled to a line 57 leading from ground 58 to an electronic switch 59. A variable resistor 61 coupled to electronic switch 59 functions as a duty cycle control. Optimization of the bone healing properties is achieved when the electronic switch 59 is turned on and off. The electronic switch 59 is turned on and off in a predetermined duty cycle. The control of the duty cycle is achieved by the adjustment of variable resistors 61 to regulate the average quantity of electrical current flowing in the tissue. Electronic switch 59 is connected in series with coil units 18 and 19. A phase-sensing resistor 62 is coupled to line 57 and coil line 23 and to a phase locked loop with a line 63. Line 63 is connected to a phase detector 64 forming a part of the phase locked loop. The output of phase detector 64 is directed to a low pass filter 65. The output of filter 65 is connected to a voltage controlled oscillator (VCO) 66. Phase detector 64, low pass filter 65, and VCO 66 make up a conventional phase locked loop circuit, such as National Semiconductor Part Number LM 1391. A variable resistor 67 connects VCO 66 with amplifier 68. Output 69 of amplifier 68 carries the output signal to electrodes 16 and 17. A feedback resistor 71 is connected with line 72 to phase detector 64.

Figure 13:
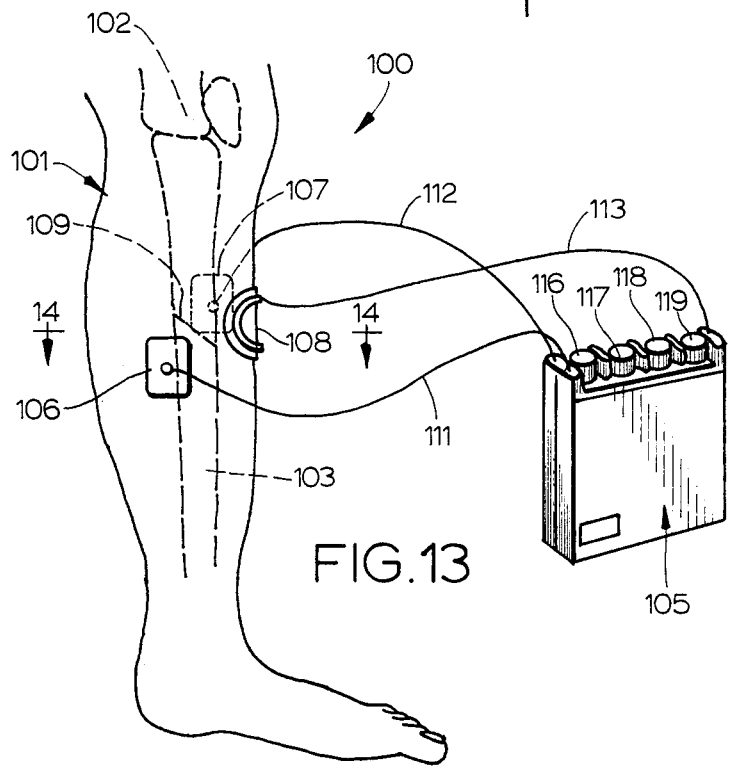
FIG. 13 is a diagrammatic view of a primate leg having a fractured tibia treated with a second embodiment of the apparatus for healing tissue of the invention.
Figure 14:
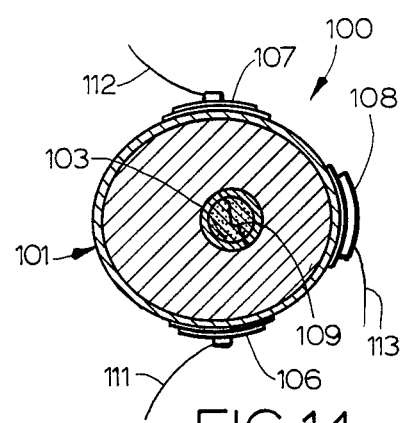
FIG. 14 is an enlarged sectional view taken along the line 14—14 of FIG. 13.

Referring to FIGS. 13 and 14, there is shown a second embodiment of the apparatus of the invention indicated generally at 100 for providing electrical treatment to enhance the healing of injured tissue, such as bone tissue, and implementing the method of healing injured tissue of the invention. Apparatus 100 is operatively associated with a primate leg 101 for enhancing the healing of a fracture in shin bone 103. Leg 101 has a thigh bone 102 and muscle and skin tissue 104 surrounding the bones 102 and 103. Apparatus 100 has a pulsed generator unit indicated generally at 105 electrically coupled to a pair of electrodes 106 and 107. Electrodes 106 and 107 are the disposable type, as shown in detail in FIGS. 3–5. A coil assembly 108 is adjacent the front of the leg about midway between the electrodes 106 and 107.

Coil assembly 108 is identical to coil assembly 18, shown in FIGS. 6–8. Electrodes 106 and 107 and coil assembly 108 are laterally disposed relative to and aligned with the fracture 109 in bone 103. Electrodes 106 and 107 are positioned on opposite sides of fracture 109 with the coil assembly 108 disposed in a circumferential relationship about 90 degrees from each electrode 106 and 107. A pair of electrical lines or cables 111 and 112 connect the electrode current output of generator 105 to the contact terminals of electrodes 106 and 107. A cable 113 connects the coil current output of the field generator to coil assembly 108. The pulse generator unit 105 has four manually operated controls comprising a pulse rate control 116, an amperage control 117, and a pulse width control 118. An additional control 119 functions to adjust the intensity of the magnetic field established by coil assembly 108. Pulse generator unit 105 corresponds to the power generator unit 15 and includes the phase synchronizing control circuit of FIG. 9.

In use, electrical current from generator means 105 is transmitted via electrodes 106 and 107 to the bone tissue. The energization of the coil assembly 108 produces a magnetic field in the region of fracture 109. The net force produced by the electrode current and magnetic field is at right angles to both the magnetic field and the direction of the current flow. The net force follows the longitudinal length of bone 103 and is generally perpendicular to the plane of the fracture in the bone.

The apparatus and method of enhancing the healing of tissue, such as a fractured bone, is not restricted to pulsed electrical currents in the electrodes and varying magnetic flux fields generated by the coil assemblies. Under some conditions, the patient requires uninterrupted currents and magnetic flux fields. The apparatus can be provided with a mode whereby a static magnetic flux field is created by constantly energizing the coil assemblies. Alternatively, a static magnetic flux field can be created with the use of one or more permanent magnets located adjacent the patient. Direct current is provided to the electrodes simultaneously with the energization of the coil assemblies. The resultant net current flows generally along the path of the injured tissue and generally normal to the plane of the injury, such as the fracture in the bone. The net current has substantial beneficial healing enhancement characteristics, as described herein.

While there has been shown and described the preferred embodiments of the method and apparatus of promoting the healing of tissue and the coil assemblies used therein, it is understood that changes in the structure, materials, electrical circuits, electrodes, and coil assemblies may be made by those skilled in the art without departing from the invention. The invention is defined in the following claims.

The embodiments of the invention in which an exclusive property or privilege is claimed are defined as follows:

1. An apparatus for promoting healing of injured tissue within a region of a living body comprising: electrode means for transcutaneously applying a current to the body which passes through the region, coil means for producing a magnetic field which passes through the region, electric current generator means for providing electric currents to said electrode means and to said coil means, and circuit means for coordinating the electric currents provided to the electrode means and the coil means to produce simultaneous presence and interaction within the region of the current from the electrode means and the magnetic field from the coil means with a spatial and polarity relationship which produces unidirectional resultant current in the region of the injured tissue in a direction generally perpendicular to the current from the electrode means and generally perpendicular to the magnetic field that enhances the healing of the injured tissue.

2. The apparatus of claim 1 wherein: said electric current generator means provides current of alternating polarity and a predetermined frequency to the electrode means and the coil means, and said circuit means includes means to maintain a predetermined phase relationship between the currents and thus between the current from the electrode means and the magnetic field so as to produce a unidirectional resultant current through the region of the injured tissue despite changes in polarity of the electrical currents from the electric current generator means.

3. The apparatus of claim 1 wherein: said current generator means comprises pulse generator means electrically connected to the electrode means for providing alternating polarity electric current pulses to said electrode means, and field generator means electrically connected to said coil means for providing alternating polarity electric current pulses to said coil means, the pulses to the electrode means and the coil means being of the same frequency and having a predetermined phase relationship so that the unidirectional resultant current is produced in the region of the injured tissue and in a direction of desired healing of the injury of said tissue.

4. The apparatus of claim 1 wherein: said electrode means comprises a pair of electrodes for attachment to skin.

5. The apparatus of claim 1 wherein: said coil means comprise a flexible body means for housing a coil and having a surface, adhesive means on said surface for attaching the flexible body means to skin, and a coil located within said flexible body means, and means for electrically connecting said coil to said generator means.

6. The apparatus of claim 5 wherein: said flexible body means comprises a flexible base having a first surface covered with the adhesive means and a second surface, said coil being located adjacent said second surface, and means mounting the coil on said flexible base.

7. The apparatus of claim 6 wherein: said base is a flexible first sheet member, and the means mounting the coil on the base comprises a flexible second sheet member covering the coil and secured to the first sheet member.

8. The apparatus of claim 1 wherein: said current generator means comprises a first means for providing electric current to said electrode means, and second means for providing electric current to said coil means thereby establishing a magnetic field.

9. The apparatus of claim 8 including: means to vary the intensities of the electric currents supplied to the electrode means and coil means.

10. The apparatus of claim 1 wherein: said current generator means includes pulse generator means for providing electric current pulses to said electrode means and said coil means, said pulse generator means having first control means to vary intensity of the current pulses supplied to said electrode means, second control means to vary a pulse rate of the current pulses supplied to said electrode means, and third control means to vary pulse amplitude of the current pulses supplied to said electrode means, said second control means being operable to set pulse intervals of both the electric current pulses supplied to said electrode means and said coil means.

11. The apparatus of claim 10 wherein: said pulse generator means includes control means to vary intensity of the electric current pulses provided to said coil means.

12. A method of treatment of injured tissue to enhance the healing thereof comprising: applying pulses of electrical current to the skin of the tissue adjacent the injured tissue, and applying, at a same frequency, a pulsed magnetic field to the injured tissue simultaneously and in a predetermined phase and spatial relationship to the pulses of electrical current which establishes as a result of interaction of the electrical current and the magnetic field a resultant unidirectional current generally perpendicular to a plane of the injured tissue to enhance the healing thereof.

13. The method of claim 12 wherein: the magnetic field is applied to the injured tissue in a direction generally normal to the application of the electrical current thereto.

14. The method of claim 12 wherein: the pulses of electric current are continuously applied to first opposite sites portions of the tissue adjacent the injured tissue, and the magnetic field pulses are applied to second opposite portions of the tissue adjacent the injured tissue.

15. The method of claim 14 wherein: said first opposite portions are located generally normal to said second opposite portions.

16. The method of claim 12 wherein: said pulses of electrical current have a square wave form, and said pulsed magnetic field has a square wave form in fixed phase relationship with the pulses of electrical current.

17. A method of treatment of a fractured bone to enhance the healing thereof comprising: transcutaneously applying pulses of electric current to a region adjacent the fracture of the bone, and applying a pulsed magnetic field to the region adjacent the fractured bone simultaneously and in fixed phase and spatial relationship with the pulses of electric current to establish a resultant unidirectional current produced by interaction of the electric current and the magnetic field which is generally perpendicular to a plane of said fracture to enhance the healing of the fracture.

18. The method of claim 17 wherein: the magnetic field is applied in a direction generally normal to the application of the electrical current thereto.

19. The method of claim 17 wherein: the pulses of electric current are applied to first opposite portions of the region adjacent the fracture, and the magnetic field forces are applied to second opposite portions of the tissue adjacent the fracture.

20. The method of claim 19 wherein: the first opposite portions are located generally normal to said second opposite portions.

21. The method of claim 17 wherein: said pulses of electrical current have a square wave form, and said pulsed magnetic field has a square wave form in fixed phase relationship with the pulses of electrical current.

22. A method of enhancing bone growth within a region of a body of an animal, the method comprising:
  positioning electrodes in contact with skin of the body on opposite sides of the body and in alignment with the region;
  positioning a magnetic field coil adjacent the skin, spatially separated from the electrodes and in alignment with the region;
  supplying a first electrical current transcutaneously through the electrodes to the body so that the first current flows through the region; and
  supplying a second electrical current to the coil to produce a magnetic field within the region which interacts with the first current to produce a resultant current within the region which is aligned generally in a direction of desired bone growth.

23. The method of claim 22 wherein the first and second electrical currents have alternating polarity, are at the same frequency, and are maintained in a predetermined phase relationship which produces a unidirectional resultant current.

24. A method of promoting bone accretion in a region within a body of an animal, the method comprising:
  providing an electrical current transcutaneously to the body in a direction which passes through the region and has a component perpendicular to the direction of desired accretion of bone; and
  providing a magnetic field which passes through the region, the magnetic field having a component perpendicular to said component of the electrical current and perpendicular to the direction of desired accretion so that the supplied electrical current and the magnetic field interact to produce a resultant current within the region of the body which has a component aligned with the direction of desired accretion of bone.

25. A method of promoting bone growth in a region within a body of an animal, the method comprising:

providing an electrical current transcutaneously to the body in a direction which passes through the region, the electrical current having an alternating polarity and a predetermined frequency; and providing a magnetic field which passes through the region in a direction generally perpendicular to the direction of the electrical current, the magnetic field having an alternating polarity, the same predetermined frequency, and having a predetermined phase and polarity relationship to the electrical current.

26. An apparatus for enhancing bone growth within a body of an animal, the apparatus comprising:

electrode means for transcutaneously applying a current to the body which passes through the region in a direction generally perpendicular to a direction of desired bone accretion;

coil means for providing a magnetic field which passes through the region in a direction generally perpendicular to the direction of desired bone accretion and generally perpendicular to the current; and means for controlling operation of the electrode means and coil means so that the current and the magnetic field are simultaneously present and interact within the region to produce a resultant current within the region which is aligned with the direction of desired bone accretion.

27. An apparatus for enhacing bone growth within a body of an animal, the apparatus comprising:

electrode means for transcutaneously applying a current of alternating polarity and a predetermined frequency to the body which passes through the region in a direction generally perpendicular to a direction of desired bone accretion;

coil means for providing a magnetic field of alternating polarity and the predetermined frequency which passes through the region in a direction perpendicular to the direction of desired bone accretion and generally perpendicular to the current; and means for controlling operation of the electrode means and coil means so that the current and the magnetic field are simultaneously present and have a predetermined phase and polarity relationship.

28. An apparatus for promoting bone growth in a region within a body of an animal, the apparatus comprising:

means for providing an electrical current transcutaneously to the body in a direction which passes through the region, the electrical current having an alternating polarity and a predetermined frequency; and means for providing a magnetic field which passes through the region in a direction generally perpendicular to the direction of the electrical current, the magnetic field having an alternating polarity, the same predetermined frequency, and having a predetermined fixed phase and polarity relationship to the electrical current.

* * * * *